US010435362B2

(12) United States Patent
Tertel et al.

(10) Patent No.: US 10,435,362 B2
(45) Date of Patent: *Oct. 8, 2019

(54) PROCESS FOR OXIDIZING ONE OR MORE THIOL COMPOUNDS AND SUBSEQUENT SEPARATION IN A SINGLE VESSEL

(71) Applicant: UOP LLC, Des Plaines, IL (US)

(72) Inventors: Jonathan A. Tertel, Mount Prospect, IL (US); Susanna K. Wong, Chicago, IL (US)

(73) Assignee: UOP LLC, Des Plaines, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/808,609

(22) Filed: Nov. 9, 2017

(65) Prior Publication Data

US 2018/0170864 A1 Jun. 21, 2018

Related U.S. Application Data

(60) Provisional application No. 62/437,506, filed on Dec. 21, 2016.

(51) Int. Cl.
| | |
|---|---|
| *C07C 319/14* | (2006.01) |
| *C07C 321/12* | (2006.01) |
| *B01D 11/04* | (2006.01) |
| *B01D 11/00* | (2006.01) |

(52) U.S. Cl.
CPC ........ *C07C 319/14* (2013.01); *B01D 11/0484* (2013.01); *B01D 11/0488* (2013.01); *B01D 11/0492* (2013.01); *B01D 2011/002* (2013.01); *C10G 2300/202* (2013.01); *C10G 2300/207* (2013.01)

(58) Field of Classification Search
None
See application file for complete search history.

(56) References Cited

U.S. PATENT DOCUMENTS

| | | | |
|---|---|---|---|
| 2,230,654 | A | 2/1941 | Plunkett |
| 4,318,825 | A | 3/1982 | Frame |
| 5,207,927 | A | 5/1993 | Marinangeli et al. |
| 5,456,661 | A | 10/1995 | Narciso |

(Continued)

FOREIGN PATENT DOCUMENTS

JP      2012162731 A      8/2012

OTHER PUBLICATIONS

Copending U.S. Appl. No. 15/846,417, filed Dec. 19, 2017 with a provisional date of Dec. 21, 2016.*

(Continued)

*Primary Examiner* — Rosalynd A Keys

(57) ABSTRACT

One exemplary embodiment can be a process for oxidizing one or more thiol compounds from an alkaline stream. The process may include passing a mixed stream having the alkaline stream to a vessel having an oxidation section, a separation section and a vent gas section. Often, the oxidation section includes a body containing one or more packing elements. The process can further include passing an oxidized alkaline stream to the separation section containing a first chamber and a second chamber. Usually, the first chamber contains a coated mesh and packing. The two sections further form a neck contains a packing, a distributor, and a mesh.

9 Claims, 2 Drawing Sheets

(56) References Cited

U.S. PATENT DOCUMENTS

| | | |
|---|---|---|
| 7,875,185 B2 | 1/2011 | Zhang |
| 8,173,856 B2 | 5/2012 | Tertel et al. |
| 8,574,429 B2 | 11/2013 | Zhang et al. |
| 9,157,032 B2 | 10/2015 | Tertel et al. |
| 2012/0000826 A1 | 1/2012 | Tertel et al. |
| 2014/0235897 A1 | 8/2014 | Tertel et al. |
| 2015/0284264 A1 | 10/2015 | Kumfer et al. |
| 2016/0263492 A1* | 9/2016 | Gao ................ B01D 3/008 |

OTHER PUBLICATIONS

Sullivan, The Role of the Merox™ Process in the Era of Ultra Low Sulfur Transportation Fuels, 5th EMEA Catalyst Technology Conference Mar. 3 & 4, 2004.
Search Report dated Feb. 7, 2018 for corresponding PCT Appl. No. PCT/US2017/062707.

\* cited by examiner

PROCESS FOR OXIDIZING ONE OR MORE THIOL COMPOUNDS AND SUBSEQUENT SEPARATION IN A SINGLE VESSEL

CROSS-REFERENCE TO RELATED APPLICATION

This application claims priority from Provisional Application No. 62/437,506 filed Dec. 21, 2016, the contents of which cited application are hereby incorporated by reference in its entirety.

FIELD OF THE INVENTION

This invention generally relates to a process for oxidizing one or more thiol compounds from an alkaline stream and separating the oil by-product and excess air from the oxidized alkaline stream within a single vessel.

DESCRIPTION OF THE RELATED ART

A sulfur removal process can extract mercaptan from a hydrocarbon stream to a caustic stream. In a sulfur extraction unit, caustic extracts mercaptan from a hydrocarbon stream. These mercaptides may then be oxidized to disulfides by adding air and catalyst, and running the stream through an oxidizer.

In a sulfur extraction unit, regenerated alkaline stream is often reused. The mercaptides in the caustic may be converted in the presence of oxygen to disulfides in an oxidizer. These three phases, spent air, lean caustic, and disulfide oil, can then be separated in a horizontal disulfide separator. Frequently, the caustic may further be contacted with a hydrocarbon to separate more disulfide oil from the caustic, requiring another vessel. Also, due to current and upcoming regulations, it is often required to contact the spent air with hydrocarbon to remove sulfur from this stream in another vessel, such as a scrubber. These vessels may require increased plot space. Moreover, the disulfide oil can be sent from the disulfide separator to a filter or water wash to remove entrained caustic prior to being sent to downstream processing. Thus, it would be desirable to reduce the number of vessels and plot space requirements for an extraction apparatus.

SUMMARY OF THE INVENTION

A first embodiment of the invention is a process for oxidizing one or more thiol compounds from an alkaline stream, and separating the oil by-product and excess air from the oxidized alkaline stream in a single vessel. The process may include passing a mixed stream comprising the alkaline stream to a vessel having an oxidation section, a dividing wall, a separation section, wherein all sections comprise one or more packing elements, the latter two sections also contain a scrubbing feature which entails a distributor, and a mesh, passing an oxidized alkaline stream over the dividing wall where the oil by-product is separated in the separation section containing a first chamber and a second chamber wherein the first chamber may contain a coated mesh and a wash oil distributor, passing a vent gas stream, also known as spent air, upwards to the neck which contains packing, a mesh and a wash oil distributor for scrubbing, and passing the vent gas stream to a vent tank. In another embodiment, the vent tank may be housed in the neck of the apparatus internally.

Definitions

As used herein, the term "stream" can include various hydrocarbon molecules, such as straight-chain, branched, or cyclic alkanes, alkenes, alkadienes, and alkynes, and optionally other substances, such as gases, e.g., hydrogen, or impurities, such as heavy metals, and sulfur and nitrogen compounds. The stream can also include aromatic and non-aromatic hydrocarbons. Moreover, the hydrocarbon molecules may be abbreviated C1, C2, C3 ... Cn where "n" represents the number of carbon atoms in the one or more hydrocarbon molecules. Furthermore, a superscript "+" or "−" may be used with an abbreviated one or more hydrocarbons notation, e.g., $C3^+$ or $C3^-$, which is inclusive of the abbreviated one or more hydrocarbons. As an example, the abbreviation "$C3^+$" means one or more hydrocarbon molecules of three carbon atoms and/or more. In addition, the term "stream" may be applicable to other fluids, such as aqueous and non-aqueous solutions of alkaline or basic compounds, such as sodium hydroxide.

As used herein, the term "zone" can refer to an area including one or more equipment items and/or one or more sub-zones. Equipment items can include one or more reactors or reactor vessels, heaters, exchangers, pipes, pumps, compressors, and controllers. Additionally, an equipment item, such as a reactor, dryer, or vessel, can further include one or more zones or sub-zones.

As used herein, the term "rich" can mean an amount of at least generally about 50%, and preferably about 70%, by weight, of a compound or class of compounds in a stream. If referring to a solute in solution, e.g., one or more disulfide compounds in an alkaline solution, the term "rich" may be referenced to the equilibrium concentration of the solute. As an example, about 5%, by mole, of a solute in a solvent may be considered rich if the concentration of solute at equilibrium is 10%, by mole.

As used herein, the term "substantially" can mean an amount of at least generally about 80%, preferably about 90%, and optimally about 99%, by weight, of a compound or class of compounds in a stream.

As used herein, the term "coupled" can mean two items, directly or indirectly, joined, fastened, associated, connected, or formed integrally together either by chemical or mechanical means, by processes including stamping, molding, or welding. What is more, two items can be coupled by the use of a third component such as a mechanical fastener, e.g., a screw, a nail, a bolt, a staple, or a rivet; an adhesive; or a solder.

As used herein, the term "coalescer" may be a device containing glass fibers or other material to facilitate separation of immiscible liquids of similar density.

As used herein, the term "immiscible" can mean two or more phases that cannot be uniformly mixed or blended.

As used herein, the term "phase" may mean a liquid, a gas, or a suspension including a liquid and/or a gas, such as a foam, aerosol, or fog. A phase may include solid particles. Generally, a fluid can include one or more gas, liquid, and/or suspension phases.

As used herein, the term "alkali" can mean any substance that in solution, typically a water solution, has a pH value greater than about 7.0, and exemplary alkali can include sodium hydroxide, potassium hydroxide, or ammonia. Such an alkali in solution may be referred to as "an alkaline solution" or "an alkaline" and includes caustic, i.e., sodium hydroxide in water.

As used herein, the term "parts per million" may be abbreviated herein as "ppm" and "weight ppm" may be abbreviated herein as "wppm".

As used herein, the term "mercaptan" typically means thiol and may be used interchangeably therewith, and can include compounds of the formula RSH as well as salts thereof, such as mercaptides of the formula RS$^-$M$^+$ where R is a hydrocarbon group, such as an alkyl or aryl group, that is saturated or unsaturated and optionally substituted, and M is a metal, such as sodium or potassium.

As used herein, the term "disulfides" can include dimethyldisulfide, diethyldisulfide, and ethylmethyldisulfide, and possibly other species having the molecular formula RSSR' where R and R' are each, independently, a hydrocarbon group, such as an alkyl or aryl group, that is saturated or unsaturated and optionally substituted. Typically, a disulfide is generated from the oxidation of a mercaptan-containing caustic and forms a separate hydrocarbon phase that is not soluble in the aqueous caustic phase. Generally, the term "disulfides" as used herein excludes carbon disulfide ($CS_2$).

As used herein, the weight percent or ppm of sulfur, e.g., "wppm-sulfur" is the amount of sulfur, and not the amount of the sulfur-containing species unless otherwise indicated. As an example, methylmercaptan, $CH_3SH$, has a molecular weight of 48.1 with 32.06 represented by the sulfur atom, so the molecule is about 66.6%, by weight, sulfur. As a result, the actual sulfur compound concentration can be higher than the wppm-sulfur from the compound. An exception is that the disulfide content in caustic can be reported as the wppm of the disulfide compound.

As used herein, the term "lean caustic" is a caustic having been treated and having desired levels of sulfur, including one or more mercaptans and one or more disulfides for treating one or more C1-C5 hydrocarbons in an extraction zone.

As used herein, the term "regeneration" with respect to a solvent stream can mean removing one or more disulfide sulfur species from the solvent stream to allow its reuse.

As depicted, process flow lines in the figures can be referred to, interchangeably, as, e.g., lines, pipes, branches, distributors, streams, effluents, feeds, products, portions, catalysts, withdrawals, recycles, suctions, discharges, and caustics.

DETAILED DESCRIPTION

Figure 1:
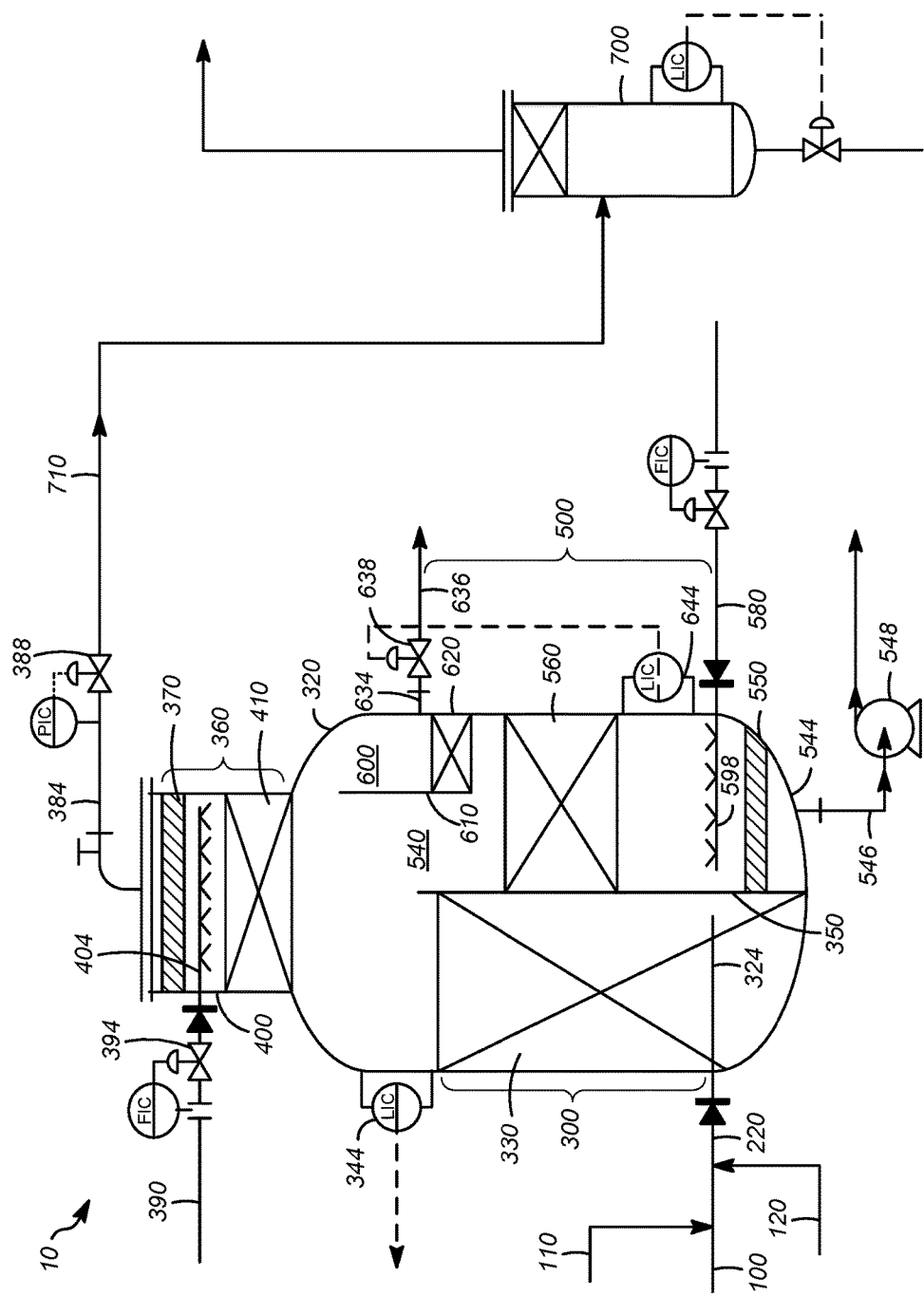
FIG. 1 is a schematic, cross-sectional depiction of an exemplary apparatus.

Referring to FIG. 1, an exemplary apparatus 10 is depicted, which may include an oxidation section 300 and a separation section 500, and a dividing wall 350. Typically, the apparatus 10 receives a mixed stream 220 comprising the alkaline stream 100, typically rich caustic which includes one or more thiol compounds, an oxygen-containing gas 110, such as air and potentially a fresh wash oil stream 120. The rich caustic can be obtained from an extraction zone to remove sulfur compounds from one or more hydrocarbons, such as one or more C2-C8 hydrocarbons. Such exemplary extraction zones are disclosed in, e.g., US 2012/0000826. The alkaline stream 100, wash oil stream 120, and an oxygen-containing gas stream 110, such as air, may enter the oxidation section 300.

The apparatus 10 can include a body 320 and a neck 360. Generally, the neck 360 can be coupled to the body 320 in any suitable manner, such as welds, or may be formed integrally together out of a common piece of sheet metal. The neck 360 may have a smaller diameter than the body 320. Often, the body 320 can include two sections 300 and 500 that consist of distributors 324 and 598, one or more packing elements 330 and 560, and level controllers 344 and 644. Typically, the distributors 324 and 598 can be any suitable device, such as a ring distributor or an elongated pipe forming a series of holes. The one or more packing elements 330 and 560 can include any suitable packing, such as at least one of ring packing, such as one or more carbon or stainless steel rings, a fiber contactor, a film contactor, one or more trays, and a mesh, to increase the surface area for improving contact between the rich caustic, catalyst, and the oxygen-containing gas. One exemplary ring packing can include rings sold under the trade designation RASCHIG by Raschig GmbH of Ludwigshafen, Germany. Alternatively, the carbon rings or a carbon bed can be impregnated with a metal phthalocyanine catalyst, as disclosed in, e.g., U.S. Pat. Nos. 4,318,825 and 5,207,927.

The neck 360 can include a mesh 370, a distributor 400, and a packing 410. Generally, the mesh 370 can be any suitable metal and can form rings or a web to facilitate coalescence of liquid. The distributor 400 can be any suitable distributor including an elongated pipe 404 forming one or more holes and be coupled to a line 390 passing through a flow control valve 394. The packing 410 can be similar to the one or more packing elements 330 described above, and include any sort of metal mesh or web, or one or more carbon rings to facilitate contacting.

The separation section 500 is on the opposite side of the oxidation section 300 separated by the dividing wall 350. The dividing wall is connected to the bottom of the apparatus. In the example shown in FIG. 1, the dividing wall extends about two-thirds of the way up towards the neck of the apparatus 10, thus leaving an opening in the apparatus above the dividing wall 350 but below the neck 360. Generally, the separation section 500 can be subdivided into a first chamber 540 and a second chamber 600. The first chamber 540 can form an outlet 544 communicating with a caustic circulation pump 548, and include one or more packed beds 560 and one or more distributors 598. Generally, the one or more packed beds 560 can include any number of suitable beds, and include one to four beds. The packed beds 560 can include any suitable packing, such as a structured packing, particularly structured metal vapor packing, or a random packing obtained from, e.g., Raschig USA, Inc. of Arlington, Tex. In addition, the first chamber 540 may include a coalescer 550, which can include one or more coalescing elements, such as at least one of a metal mesh that is optionally coated, one or more glass fibers, sand, or anthracite coal. In one exemplary embodiment, the coalescer 550 can include a coated mesh. Desirably, the coating may be an oleophilic and/or hydrophobic coating usually suited for an aqueous phase. Such a coating may include at least one of a fluoropolymer and polypropylene. Suitable fluoropolymers can include one or more of polytetrafluoroethylene, fluorinated ethylene-propylene, perfluoroalkoxy, and ethylene tetrafluoroethylene. Exemplary fluoropolymers are disclosed in U.S. Pat. Nos. 5,456,661 and 2,230,654. The one or more distributors 580 and a second distributor 598 can take any suitable form, such as a ring or an elongated pipe forming one or more holes.

The second chamber 600 can include a lower end 610 and contain a coalescer 620. The coalescer 620 may include one or more coalescing elements, such as at least one of a metal mesh that is optionally coated, one or more glass fibers, sand, or anthracite coal. In one exemplary embodiment, the coalescer 620 can include a coated mesh. Desirably, the coating may be an oleophobic and/or hydrophilic coating usually suited for an oil phase. One exemplary mesh may include a coating sold under the trade designation COALEX or KOCH-OTTO YORK™ separations technology by Koch-Glitsch, LP of Wichita, Kans. Alternatively, the mesh can include stainless steel or fiberglass.

In operation, referring to FIG. 1, generally the alkaline stream 100, typically operates at a temperature of about 35° to about 55° C. and a pressure of about 340 kPa to about 630 kPa, is joined by an oxygen-containing gas stream 110 via a tee fitting wherein a fresh wash oil stream 120 may join upstream or downstream of this junction. Often, the oxygen-containing gas, having an oxygen content of about 5 to about 30%, by mole, oxygen. The oxygen-containing gas can include air or oxygen enriched air up to about 30%, by mole, oxygen.

The mixed stream 220 can enter the oxidation section 300 via the distributor 324. The caustic, wash oil, and air may exit the distributor 324 and rise through the one or more packing elements 330 providing sufficient surface area for an oxidation reaction with contacting of the oxygen and caustic. The caustic and disulfide oil/wash oil can exit the oxidation section 300. Typically, the spent air disengages from the liquid and passes up through the packing 410, where the spent air counter-currently may contact a wash oil stream 390 that may be passed through a valve 394 and enter via the distributor 404 to remove disulfide oil from the spent air. The wash oil stream 390 may include a hydrotreated heavy naphtha, kerosene, or diesel oil with little or no sulfur. Generally, it is preferable that the wash oil stream 390 has less than about 10 ppm, preferably less than about 1 ppm, by weight, of sulfur, as disclosed in, e.g., U.S. Pat. No. 8,173,856. Gases can rise upward and pass through the packing 410 and be contacted with a wash oil stream 390. The wash oil can fall downward contacting the gas to remove any sulfur compounds therein while the gas can continue to rise upward and pass through the mesh 370. Often, the gas must travel through the mesh 370 before exiting the gas scrubbing section 360. Preferably, any liquid can coalesce as droplets on the mesh 370 and drop back into the body 320. The spent air stream 384 may be regulated via a pressure control valve 388. The wash oil can aid the separation of disulfide compounds.

Usually, the sulfur compounds within the caustic can be converted to one or more disulfide compounds. A liquid/gas interface may occur at the top of the one or more packing elements 330. Oxidized caustic containing wash oil and disulfide oil can flow over the dividing wall 350 to the separation section 500. The liquid/gas interface can be measured with the level indicator 344 and optionally controlled by controlling the rich caustic flow coming to the body (stream 100).

The mixed liquid enters the separation section 500 with liquid falling in the first chamber 540. The separation section 500 may operate at a temperature of no more than about 60° C., and a pressure of about 250 kPa to about 500 kPa, preferably about 350 kPa to about 450 kPa. Usually, a couple of interfaces may be formed, namely a liquid-liquid interface of caustic and oil, and an air-liquid interface in the neck 360. Gases can rise from the air-liquid interface and pass through the mesh 370 that can coalesce any liquids. Generally, the total sulfur in the combined stream 384 can be no more than about 100 ppm, by weight, but may be more than about 1 ppm sulfur, by weight. As such, the gas can be sent to a vent tank if subsequently provided to a fired heater, or to a carbon canister.

The oxidized caustic containing two phases, namely caustic and wash and disulfide oils, can fall and pass through the packed beds 560. Simultaneously, a wash oil stream 580 can exit through the second distributor 598 and rise, thereby contacting the caustic and removing the majority of disulfides. Additionally, the caustic can continue to further drop in the body and pass through the coalescer 550 further separating the oil from the caustic. A regenerated caustic can pass via the outlet 544 as a regenerated alkaline stream 546 substantially free of disulfide oil and sulfur compounds. The regenerated alkaline stream 546 can be regulated by a flow control valve downstream of the caustic circulation pumps 548.

The wash and disulfide oils can rise and pass through the lower end of the second chamber 600 and then pass through the coalescer 620. In one exemplary embodiment, the mesh 620 can be at any suitable location, and may be a distance of at least one diameter of the separation section 500 above. The coalescer 620 can coalesce out any caustic that can fall downward to the first chamber 540 within the separation section 500. Oils can rise within the second chamber 600 and exit through an outlet 634. A level control valve 638 can communicate with a level controller 644 at the liquid-liquid interface to regulate the amount of the hydrocarbon or oil stream 636 substantially free of caustic, such as less than about 1 wppm of caustic, that can exit the second chamber 600 and be sent to downstream processing without requiring further filtering or washing to remove caustic.

In one embodiment, the vent tank 700 is downstream from the apparatus 10. As shown in FIG. 1, the spent air stream 384 is regulated via a pressure control valve 388 is sent to the vent tank 700 via stream 710. The spent air stream 710 passes through the vent tank 700 where any entrained wash and disulfide oils are removed before going to a nearby firebox of a fired heater. In another embodiment, the vent tank 700 is contained within the neck 360 of the apparatus 10 by elongating the disengaging space above the mesh 370.

Figure 2:
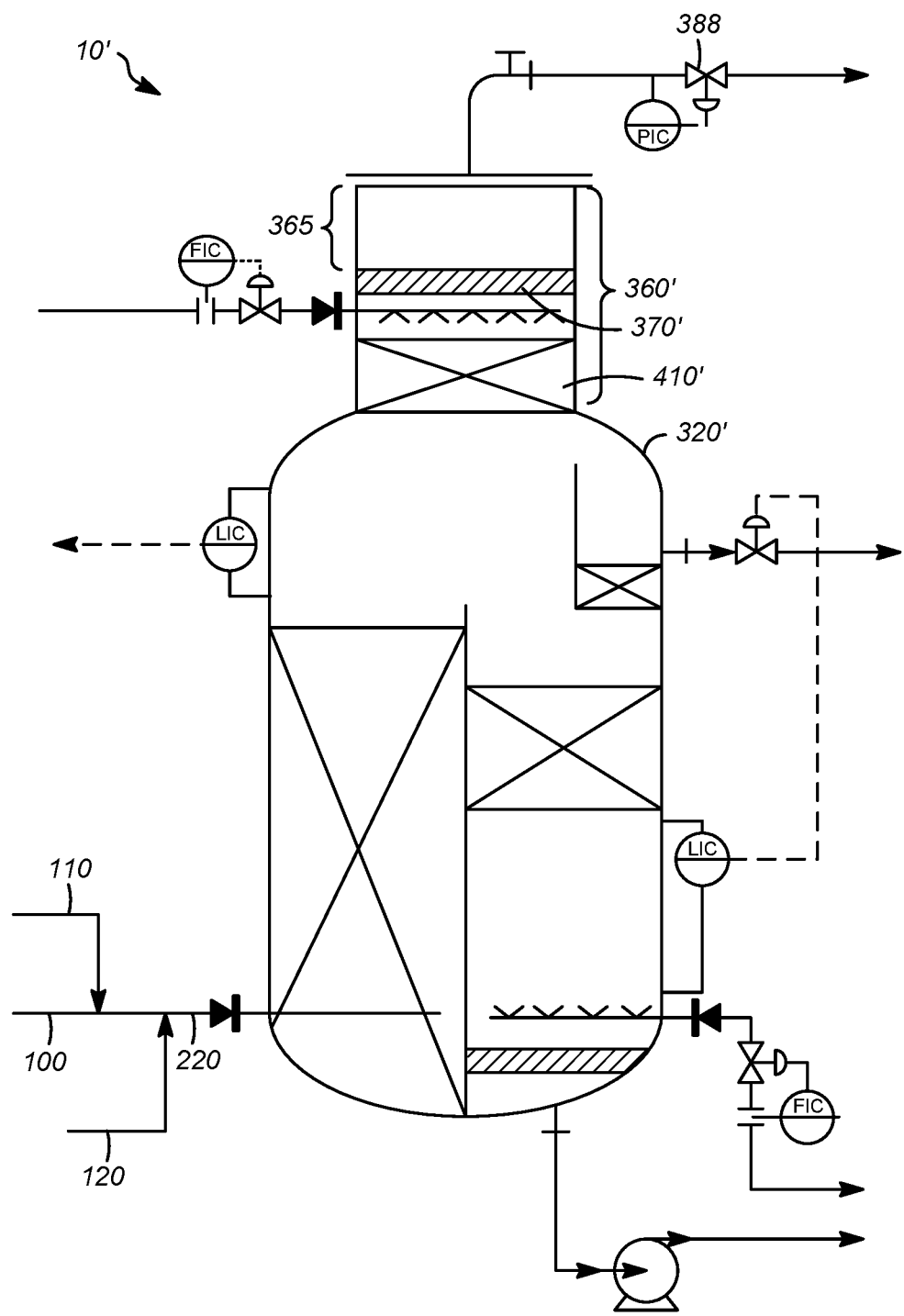
FIG. 2 is a schematic, cross-sectional depiction of another exemplary apparatus.

In this second embodiment 10' as illustrated in FIG. 2, the spent air would pass through the mesh 370', through an extended disengaging space in 365, which functions as the vent tank. In the embodiment illustrated in FIG. 2, no vent tank is needed, as there is in FIG. 1 because the added disengaging space above the top mesh blanket will allow further separation between caustic and spent air, essentially function as the vent tank. This additional space may be open as shown in FIG. 2 or may include mesh blankets (coated or uncoated) or some other packing to facilitate separation of liquid from gas. The spent air would leave the apparatus 10', thereby passing through the pressure control value 388, and on to the nearby firebox of the fired heater.

Specific Embodiments

While the following is described in conjunction with specific embodiments, it will be understood that this description is intended to illustrate and not limit the scope of the preceding description and the appended claims.

A first embodiment of the invention is a process for oxidizing one or more thiol compounds from an alkaline stream, and separating the oil by-product and excess air from the oxidized alkaline stream in a single vessel, comprising (A) passing a mixed stream comprising the alkaline stream to a vessel having an oxidation section, a dividing wall, a separation section, wherein all sections comprise one or more packing elements, the latter two sections also contain a scrubbing feature which entails a distributor, and a mesh; (B) passing an oxidized alkaline stream over the dividing wall where the oil by-product is separated in the separation section containing a first chamber and a second chamber wherein the first chamber contains a coated mesh and a wash oil distributor; (C) passing a vent gas stream, also known as spent air, upwards to the neck which contains packing, a mesh and a wash oil distributor for scrubbing; and (D) passing the vent gas stream to a vent tank. An embodiment of the invention is one, any or all of prior embodiments in this paragraph up through the first embodiment in this paragraph, wherein the vessel is at a temperature of about 35° C. to about 55° C. An embodiment of the invention is one, any or all of prior embodiments in this paragraph up through the first embodiment in this paragraph, wherein the vessel is at a pressure of about 340 kPa to about 630 kPa. An embodiment of the invention is one, any or all of prior embodiments in this paragraph up through the first embodiment in this paragraph, wherein the mesh in the neck comprises any suitable metal. An embodiment of the invention is one, any or all of prior embodiments in this paragraph up through the first embodiment in this paragraph, wherein the separation section comprises a two-chamber body. An embodiment of the invention is one, any or all of prior embodiments in this paragraph up through the first embodiment in this paragraph, wherein the packing comprises at least one of a ring packing, a fiber contactor, a film contactor, and one or more trays. An embodiment of the invention is one, any or all of prior embodiments in this paragraph up through the first embodiment in this paragraph, further comprising passing a spent oxygen-containing gas through the packing and then the mesh contained in the neck of the vessel. An embodiment of the invention is one, any or all of prior embodiments in this paragraph up through the first embodiment in this paragraph, wherein the first chamber can include one or more packing beds and one or more distributors. An embodiment of the invention is one, any or all of prior embodiments in this paragraph up through the first embodiment in this paragraph, wherein the second chamber comprises a coated mesh.

A second embodiment of the invention is an apparatus, comprising (A) a vessel having an oxidation section, a dividing wall, a separation section, and an elongated neck as the vent gas section, wherein all sections comprise one or more packing elements, the latter two sections also contain a scrubbing feature which entails a distributor, and a mesh; and (B) the separation section contains a first chamber and a second chamber wherein the first chamber contains a coated mesh; and (C) the vent gas section, or the neck of the vessel, contains packing, a mesh, and a wash oil distributor for scrubbing. An embodiment of the invention is one, any or all of prior embodiments in this paragraph up through the second embodiment in this paragraph, wherein the first chamber of the separation section contains one or more packed beds for contacting a caustic and wash oil and one or more distributors. An embodiment of the invention is one, any or all of prior embodiments in this paragraph up through the second embodiment in this paragraph, wherein the oxidation and separation sections further form a neck containing packing for contacting a vent gas and wash oil, one or more distributors, and a mesh through which one or more gases must travel before exiting the vessel. An embodiment of the invention is one, any or all of prior embodiments in this paragraph up through the second embodiment in this paragraph, wherein the first chamber forms an outlet for a regenerated alkaline stream and the second chamber forms an outlet for a hydrocarbon stream.

Without further elaboration, it is believed that one skilled in the art can, using the preceding description, utilize the present invention to its fullest extent. The preceding preferred specific embodiments are, therefore, to be construed as merely illustrative, and not limitative of the remainder of the disclosure in any way whatsoever. In the foregoing, all temperatures are set forth in degrees Celsius and, all parts and percentages are by weight, unless otherwise indicated. From the foregoing description, one skilled in the art can easily ascertain the essential characteristics of this invention and, without departing from the spirit and scope thereof, can make various changes and modifications of the invention to adapt it to various usages and conditions.

The invention claimed is:

1. A process for oxidizing one or more thiol compounds from an alkaline stream, and separating the oil by-product and excess air from the oxidized alkaline stream in a single vessel, comprising:
   (A) passing a mixed stream comprising the alkaline stream to a vessel having an oxidation section, a dividing wall attached to a bottom of the vessel and extending upward a portion the vessel's height, a separation section, wherein all sections comprise one or more packing elements, the latter two sections also contain a scrubbing feature which entails a distributor, and a mesh;
   (B) passing an oxidized alkaline stream over the dividing wall where the oil by-product is separated in the separation section containing a first chamber and a second chamber wherein the first chamber contains a coated mesh and a wash oil distributor;
   (C) passing a vent gas stream, also known as spent air, upwards to the neck which contains packing, a mesh and a wash oil distributor for scrubbing; and
   (D) passing the vent gas stream to a vent tank.

2. The process according to claim 1, wherein the vessel is at a temperature of about 35° C. to about 55° C.

3. The process according to claim 1, wherein the vessel is at a pressure of about 340 kPa to about 630 kPa.

4. The process according to claim 1, wherein the mesh in the neck comprises any suitable metal.

5. The process according to claim 1, wherein the separation section comprises a two-chamber body.

6. The process according to claim 1, wherein the packing comprises at least one of a ring packing, a fiber contactor, a film contactor, and one or more trays.

7. The process according to claim 1, further comprising passing a spent oxygen-containing gas through the packing and then the mesh contained in the neck of the vessel.

8. The process according to claim 1, wherein the first chamber can include one or more packing beds and one or more distributors.

9. The process according to claim 1, wherein the second chamber comprises a coated mesh.

* * * * *